(12) United States Patent
Gofman et al.

(10) Patent No.: US 10,897,503 B2
(45) Date of Patent: *Jan. 19, 2021

(54) SETUP SYNCHRONIZATION APPARATUS AND METHODS FOR END USER MEDICAL DEVICES

(71) Applicant: ASCENSIA DIABETES CARE HOLDINGS AG, Basel (CH)

(72) Inventors: Igor Gofman, Croton-on-Hudson, NY (US); Christopher Dionisio, Millington, NJ (US)

(73) Assignee: Ascensia Diabetes Care Holdings AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/546,096

(22) Filed: Aug. 20, 2019

(65) Prior Publication Data

US 2019/0373059 A1 Dec. 5, 2019

Related U.S. Application Data

(63) Continuation of application No. 15/110,740, filed as application No. PCT/US2014/069628 on Dec. 10, 2014, now Pat. No. 10,432,717.

(Continued)

(51) Int. Cl.
*H04L 29/08* (2006.01)
*A61B 5/00* (2006.01)
(Continued)

(52) U.S. Cl.
CPC .......... *H04L 67/1095* (2013.01); *A61B 5/002* (2013.01); *A61B 5/0022* (2013.01);
(Continued)

(58) Field of Classification Search
CPC . H04L 65/1069; H04L 67/1095; G16H 40/63; A61B 5/002; A61B 5/0022;
(Continued)

(56) References Cited

U.S. PATENT DOCUMENTS 6,540,672 B1  4/2003  Simonsen
6,569,094 B2  5/2003  Suzuki et al.
(Continued)

FOREIGN PATENT DOCUMENTS

CN  1348558 A  5/2002
CN  1921529 A  2/2007
(Continued)

OTHER PUBLICATIONS

Chinese Office Action of related Chinese Application No. 201480076629.2 dated Sep. 9, 2019.
(Continued)

*Primary Examiner* — Kostas J Katsikis
(74) *Attorney, Agent, or Firm* — Dugan & Dugan, PC

(57) ABSTRACT

Embodiments of the present invention enable setup synchronization of an end user medical device such as a blood glucose meter. Some embodiments may include a controller including a memory; a transceiver operatively coupled to the controller; and a host computer interface operative to couple the controller to a host computer, wherein the memory is operative to store instructions executable on the controller. The instructions are adapted to cause the controller to scan for an advertising medical device using the transceiver, establish a communications connection with a medical device advertising for synchronization, and transmit synchronization data to a medical device once a communication connection has been estabilshed. Numerous other aspects are disclosed.

20 Claims, 4 Drawing Sheets

Related U.S. Application Data

(60) Provisional application No. 61/926,215, filed on Jan. 10, 2014.

(51) Int. Cl.
  *A61B 5/145* (2006.01)
  *G16H 40/63* (2018.01)
  *H04L 29/06* (2006.01)

(52) U.S. Cl.
  CPC .......... *A61B 5/14532* (2013.01); *A61B 5/742* (2013.01); *G16H 40/63* (2018.01); *H04L 65/1069* (2013.01); *A61B 2560/0271* (2013.01); *A61B 2560/0487* (2013.01)

(58) Field of Classification Search
  CPC ................ A61B 5/742; A61B 5/14532; A61B 2560/0271; A61B 2560/0487
  See application file for complete search history.

(56) References Cited

U.S. PATENT DOCUMENTS

| | | | |
|---|---|---|---|
| 6,604,050 B2 | 8/2003 | Trippel et al. | |
| 6,607,484 B2 | 8/2003 | Suzuki et al. | |
| 6,674,821 B1 | 1/2004 | Mejyr | |
| 6,790,178 B1 | 9/2004 | Mault et al. | |
| 6,802,812 B1 | 10/2004 | Walker | |
| 6,819,013 B2 | 11/2004 | Kelly et al. | |
| 6,870,475 B2 | 3/2005 | Fitch et al. | |
| 7,286,894 B1 | 10/2007 | Grant et al. | |
| 7,316,648 B2 | 1/2008 | Kelly et al. | |
| 7,549,961 B1 | 6/2009 | Hwang | |
| 7,779,183 B2 | 8/2010 | Koehler et al. | |
| 8,131,564 B2 | 3/2012 | Dicks | |
| 8,208,973 B2 | 6/2012 | Mehta | |
| 8,483,974 B2 | 7/2013 | Connolly | |
| 8,579,813 B2 | 11/2013 | Causey et al. | |
| 8,682,598 B2 | 3/2014 | Connolly et al. | |
| 8,755,053 B2 | 6/2014 | Fright | |
| 8,758,245 B2 | 6/2014 | Ray et al. | |
| 8,844,007 B2 * | 9/2014 | Vicente .................... | H04W 4/70 726/6 |
| 8,895,316 B2 | 11/2014 | Batman et al. | |
| 8,954,007 B2 | 2/2015 | Hillyard | |
| 9,179,844 B2 | 11/2015 | Fright | |
| 9,445,445 B2 * | 9/2016 | Miller ................. | G01N 27/3271 |
| 9,462,623 B2 | 10/2016 | Jakusovszky | |
| 9,696,980 B2 | 7/2017 | Dicks | |
| 9,750,896 B2 | 9/2017 | Kamen | |
| 9,861,285 B2 | 1/2018 | Fright | |
| 9,901,292 B2 * | 2/2018 | Hernandez-Rosas ........................ | H04W 76/34 |
| 10,226,205 B2 * | 3/2019 | Hernandez-Rosas ........................ | A61B 5/14532 |
| 10,432,717 B2 * | 10/2019 | Gofman .............. | H04L 65/1069 |
| 2001/0038343 A1 | 11/2001 | Meyer et al. | |
| 2006/0009697 A1 | 1/2006 | Banet et al. | |
| 2006/0106433 A1 | 5/2006 | Mazar et al. | |
| 2006/0273930 A1 | 12/2006 | Godden | |
| 2007/0003061 A1 | 1/2007 | Jung et al. | |
| 2007/0027388 A1 | 2/2007 | Chou | |
| 2007/0181425 A1 | 8/2007 | Kim | |
| 2007/0293910 A1 | 12/2007 | Strother et al. | |
| 2007/0299480 A1 | 12/2007 | Hill | |
| 2008/0092638 A1 | 4/2008 | Brennenman et al. | |
| 2008/0109302 A1 | 5/2008 | Salokannel et al. | |
| 2009/0069642 A1 | 3/2009 | Gao et al. | |
| 2009/0116479 A1 | 5/2009 | Choi | |
| 2009/0163793 A1 | 6/2009 | Koehler | |
| 2009/0198141 A1 | 8/2009 | Hollinger et al. | |
| 2009/0213213 A1 | 8/2009 | Fright | |
| 2009/0243791 A1 | 10/2009 | Partin | |
| 2010/0000862 A1 | 1/2010 | Rao | |
| 2010/0111066 A1 | 5/2010 | Mehta | |
| 2010/0113897 A1 | 5/2010 | Brennenman et al. | |
| 2010/0165795 A1 | 7/2010 | Elder | |
| 2010/0228111 A1 | 9/2010 | Friman | |
| 2010/0278345 A1 | 11/2010 | Alsina et al. | |
| 2011/0060530 A1 * | 3/2011 | Fennell ................ | A61B 5/1473 702/19 |
| 2011/0066044 A1 | 3/2011 | Moon | |
| 2011/0117841 A1 | 5/2011 | Thorn | |
| 2011/0126188 A1 | 5/2011 | Bernstein | |
| 2011/0165865 A1 | 7/2011 | Gao et al. | |
| 2011/0256024 A1 | 10/2011 | Cole et al. | |
| 2011/0319813 A1 | 12/2011 | Kamen | |
| 2012/0019379 A1 | 1/2012 | Ben Ayed | |
| 2012/0052802 A1 | 3/2012 | Kasslin et al. | |
| 2012/0078071 A1 * | 3/2012 | Bohm ................ | A61B 5/14532 600/345 |
| 2012/0123227 A1 | 5/2012 | Sun et al. | |
| 2012/0149245 A1 | 6/2012 | Ralston et al. | |
| 2012/0150556 A1 | 6/2012 | Galasso | |
| 2012/0235823 A1 * | 9/2012 | Trock .................... | H01M 16/00 340/636.1 |
| 2012/0238851 A1 | 9/2012 | Kamen | |
| 2012/0245447 A1 * | 9/2012 | Karan .................... | G16H 40/63 600/365 |
| 2012/0260323 A1 * | 10/2012 | San Vicente ......... | A61B 5/1495 726/6 |
| 2012/0303638 A1 | 11/2012 | Bousamra | |
| 2013/0035575 A1 * | 2/2013 | Mayou ............... | A61B 5/14532 600/365 |
| 2013/0059541 A1 * | 3/2013 | Sloan .................... | G06Q 10/00 455/41.2 |
| 2013/0078912 A1 * | 3/2013 | San Vicente ......... | A61B 5/0026 455/39 |
| 2013/0172709 A1 * | 7/2013 | Mears ................. | G06F 19/3468 600/365 |
| 2013/0190674 A1 | 7/2013 | Case | |
| 2013/0203351 A1 * | 8/2013 | Hillan ...................... | H04B 5/00 455/41.1 |
| 2014/0012117 A1 | 1/2014 | Mensinger | |
| 2014/0149742 A1 | 5/2014 | Yau | |
| 2014/0206972 A1 * | 7/2014 | Hayter ................. | A61B 5/0004 600/365 |
| 2014/0218496 A1 * | 8/2014 | Park ..................... | A61B 5/7465 348/77 |
| 2014/0266607 A1 | 9/2014 | Olodort | |
| 2014/0273821 A1 * | 9/2014 | Miller .................. | H04B 5/0031 455/41.1 |
| 2014/0324445 A1 | 10/2014 | Carlsgaard | |
| 2014/0364056 A1 | 12/2014 | Belk | |
| 2014/0380218 A1 | 12/2014 | Refvik | |
| 2015/0123810 A1 * | 5/2015 | Hernandez-Rosas ........................ | A61B 5/14503 340/870.02 |
| 2015/0123811 A1 * | 5/2015 | Hernandez-Rosas ........................ | H04W 76/14 340/870.02 |
| 2015/0123812 A1 * | 5/2015 | Hernandez-Rosas ........................ | H04W 76/14 340/870.02 |
| 2015/0123813 A1 * | 5/2015 | Hernandez-Rosas ........................ | A61B 5/14503 340/870.02 |
| 2015/0189461 A1 | 7/2015 | Pang et al. | |
| 2016/0088372 A1 * | 3/2016 | Hernandez-Rosas ........................ | A61B 5/0004 340/870.07 |
| 2016/0089066 A1 * | 3/2016 | Hernandez-Rosas ........................ | A61B 5/14503 340/870.07 |
| 2016/0095148 A1 * | 3/2016 | Hernandez-Rosas ........................ | A61B 5/742 455/41.2 |
| 2016/0337448 A1 * | 11/2016 | Gofman ................ | A61B 5/742 |
| 2017/0030889 A1 | 2/2017 | Yao et al. | |
| 2017/0038847 A1 | 2/2017 | Schorsch | |
| 2017/0201931 A1 | 7/2017 | Swanzey et al. | |
| 2017/0208425 A1 | 7/2017 | Fu et al. | |

(56) References Cited

U.S. PATENT DOCUMENTS

| | | | |
|---|---|---|---|
| 2017/0214780 | A1 | 7/2017 | Gofman et al. |
| 2017/0344718 | A1 | 11/2017 | Chen |
| 2018/0075200 | A1* | 3/2018 | Davis .................. G16H 40/67 |
| 2018/0125397 | A1* | 5/2018 | Hernandez-Rosas ................. H04W 76/14 |
| 2018/0137937 | A1 | 5/2018 | Gass et al. |
| 2019/0373059 | A1* | 12/2019 | Gofman ............. H04L 67/1095 |

FOREIGN PATENT DOCUMENTS

| | | |
|---|---|---|
| CN | 101193586 A | 6/2008 |
| CN | 101461969 A | 6/2009 |
| CN | 101675900 A | 3/2010 |
| CN | 201491011 U | 5/2010 |
| CN | 101816170 | 8/2010 |
| CN | 202075262 U | 12/2011 |
| CN | 102422657 | 4/2012 |
| CN | 102565413 A | 7/2012 |
| CN | 202838653 U | 3/2013 |
| CN | 203311607 | 5/2013 |
| CN | 101431456 | 7/2014 |
| CN | 205006870 U | 2/2016 |
| EP | 2741 528 A1 | 6/2014 |
| JP | 2003114859 A | 4/2003 |
| JP | 2006-522346 | 9/2006 |
| JP | 2007-111514 | 5/2007 |
| JP | 2008302000 A | 12/2008 |
| JP | A2009-188764 | 8/2009 |
| JP | 2013-201516 | 10/2013 |
| JP | A2014-110636 | 6/2014 |
| JP | 2012199663 A | 1/2016 |
| TW | 201322167 A | 6/2013 |
| WO | WO0152727 | 7/2001 |
| WO | WO 2008/153825 | 12/2008 |
| WO | WO 2009/006486 | 1/2009 |
| WO | WO 2013066362 | 5/2013 |
| WO | WO2014088234 | 6/2014 |
| WO | WO 2014/146021 | 9/2014 |
| WO | WO 2015/157582 | 10/2015 |
| WO | WO 2016/007186 | 1/2016 |
| WO | WO 2016/007187 | 1/2016 |
| WO | WO 2016/007188 | 1/2016 |
| WO | WO 2016/174206 | 11/2016 |

OTHER PUBLICATIONS

Sun et al., U.S. Appl. No. 12/944,259, filed Nov. 11, 2010 (Now Published as 2012-0123227).

International Search Report and Written Opinion of related International Application No. PCT/US14/69628 dated Mar. 11, 2015.

International Search report of related International Application No. PCT/US2014/062404 dated Mar. 5, 2015.

International Search Report and Written Opinion of related International Application No. PCT/US2014/062433 dated Mar. 23, 2015.

Mare, Shrirang, et al. "ZEBRA: Zero-Effort Bilateral Recurring Authentication", 2014 IEEE Symposium on Security and Privacy, IEEE, May 18, 2014, pp. 705-720.

Mayrhofer, R., et al., "Shake Well before Use: Inituitive and Securing Pairing of Mobile Devices", IEEE Transactions on Mobile Computing, IEEE Service Center, Los Alamitos, CA, US, vol. 8, No. 6, Jun. 1, 2009, pp. 792-806.

International Search Report and Written Opinion of related International Application No. PCT/US2014/062472 dated Mar. 23, 2015.

International Search Report and Written Opinion of related International Application No. PCT/US2015/025213 dated Jun. 15, 2015.

International Preliminary Report on Patentability of related International Application No. PCT/US14/69628 dated Jul. 21, 2016.

International Preliminary Report on Patentability of related International Application No. PCT/US2015/025213 dated Oct. 20, 2016.

Gofman et al., U.S. Appl. No. 15/324,649, titled: "Improved Device Pairing With a Dual Use Piezoelectric Acoustic Component and Vibration Sensor," filed Jan. 6, 2017 (Now Published as 2017-0214780).

Fu et al., U.S. Appl. No. 15/324,632, titled: "Improved Device Pairing Taking Into Account at Least One Condition," filed Jan. 6, 2017 (Now published as 2017-0208425).

Swanzey et al., U.S. Appl. No. 15/324,654, titled: "Methods and Apparatus for Improved Low Energy Data Communications ," filed Jan. 6, 2017 (Now Published as 2017-0201931).

International Preliminary report on Patentability of related International Application No. PCT/US2014/062404 dated Jan. 19, 2017.

International Preliminary Report on Patentability of related International Application No. PCT/US2014/062472 dated Jan. 19, 2017.

International Preliminary Report on Patentability of related International Application No. PCT/US2014/062433 dated Jan. 19, 2017.

International Search Report and Written Opinion of related International Application No. PCT/EP2016/059616 dated Jun. 2, 2016.

International Preliminary Report on Patentability of related International Application No. PCT/EP2016/059616 dated Nov. 9, 2017.

Chinese Search report of related Chinese Application No. 201580031100.3 dated Jul. 19, 2018.

Japanese Office Action of related Japanese Application No. 2016-545801 dated Jul. 30, 2018.

Taiwan Search report of related Taiwan Application No. 103143687 dated Sep. 17, 2018.

Chinese Search report of related Chinese Application No. 201480076629.2 dated Dec. 11, 2018.

Chinese Search report of related Chinese Application No. 201480076629.2 dated May 31, 2019.

Chinese Office Action of Chinese Application No. 201480080414.8 dated Jul. 24, 2019.

Chinese Search report of Chinese Application No. 201480080414.8 dated Jul. 16, 2019.

\* cited by examiner

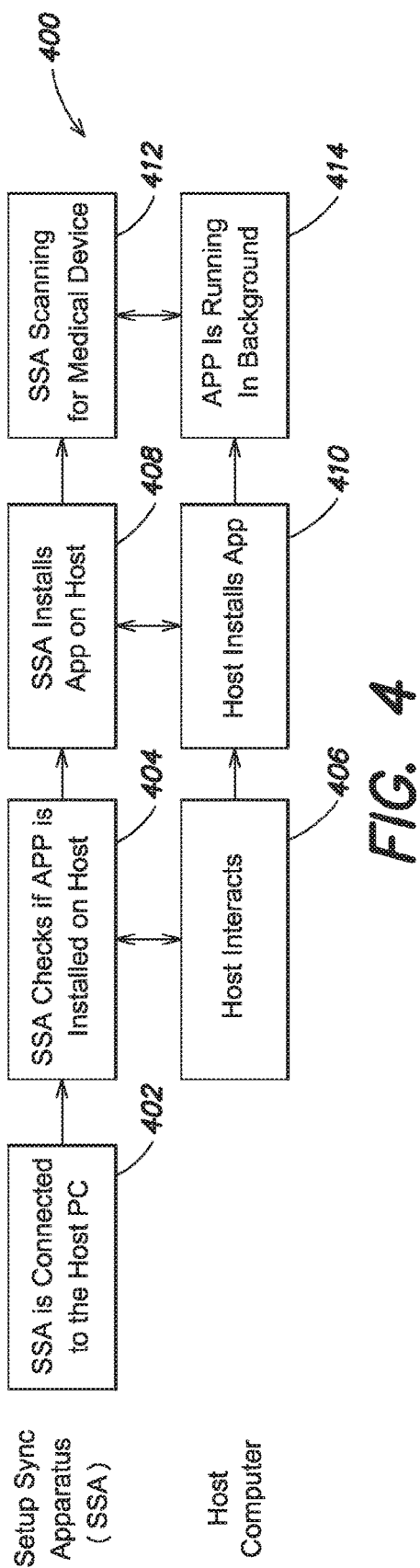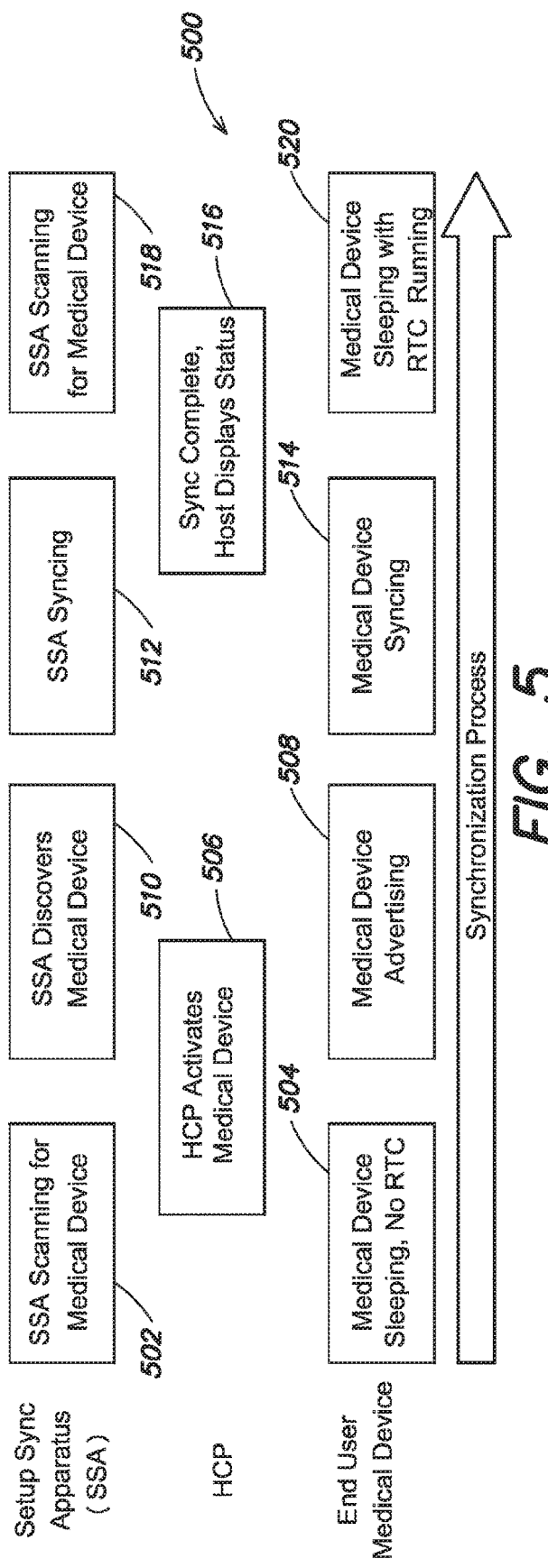

SETUP SYNCHRONIZATION APPARATUS AND METHODS FOR END USER MEDICAL DEVICES

RELATED APPLICATIONS

This is a continuation of U.S. patent application Ser. No. 15/110,740, filed Jul. 9, 2016, now U.S. Pat. No. 10,432,717, which is a 371 of International Patent Application No. PCT/US2014/069628, filed Dec. 10, 2014, which claims the benefit of U.S. Provisional Patent Application No. 61/926,215, filed Jan. 10, 2014, each of which is hereby incorporated herein by reference in its entirety for all purposes.

FIELD

The present invention relates to medical devices, and more specifically to apparatus, systems, and methods for setup synchronization of medical devices.

BACKGROUND

Conventional end user medical devices such as blood glucose meters (BGMs) are typically packaged by manufacturers with an initial configuration that may not always be optimal for the intended application or patient. Thus, frequently, a healthcare provider (HCP) must adjust the configuration of the meter. Accordingly, systems, apparatus, and methods for facilitating setup of such devices are needed.

SUMMARY

In some aspects, embodiments of the present invention provide an apparatus for setup synchronization of a medical device such as a blood glucose meter. The apparatus includes a controller including a memory; a transceiver operatively coupled to the controller; and a host computer interface operative to couple the controller to a host computer, wherein the memory is operative to store instructions executable on the controller, the instructions adapted to cause the controller to scan for an advertising medical device using the transceiver, establish a communications connection with a medical device advertising for synchronization, and transmit synchronization data to a medical device once a communication connection has been established.

In other aspects, embodiments of the present invention provide a system for setup synchronization of a medical device such as a blood glucose meter. The system includes an end user medical device including an activation function for putting the medical device in an advertising mode for requesting synchxonization; and a setup synchronization apparatus including a controller including a memory; a transceiver operatively coupled to the controller; and a host computer interface operative to couple the controller to a host computer. The memory is operative to store instructions executable on the controller, the instructions adapted to cause the controller to scan for an advertising medical device using the transceiver.

In yet other aspects, embodiments of the present invention provide a method for setup synchronization of a medical device such as a blood glucose meter. The method includes scanning for an end user medical device advertising for synchronization using a setup synchronization apparatus; discovering an end user medical device advertising for synchronization; establishing a communication connection with a discovered end user medical device; and synchronizing the connected end user medical device.

Numerous other aspects are provided in accordance with these and other embodiments of the invention. Other features and aspects of embodiments of the present invention will become more fully apparent from the following detailed description, the appended claims, and the accompanying drawings.

BRIEF DESCRIPTION OF THE DRAWINGS

FIG. 4 illustrates a block diagram representation of a system initiation process according to some embodiments of the present invention.

FIG. 5 illustrates a block diagram representation of a synchronization process according to some embodiments of the present invention.

DETAILED DESCRIPTION

End user medical devices such as, for example, blood glucose meters (BGMs) are typically provided to patients by a healthcare provider (HCP). The HCP can stock a number of devices as packaged by the manufacturer and provide the devices to patients as needed. Such devices can include a real-time clock (RTC) that conventionally is set by the manufacturer before the devices are packaged. This ensures that the end user receives a device with an accurately set RTC so that medical data can be correctly time indexed. Thus, the RTC is typically running while the device is in storage. Since the storage time for such devices can be as long as fifteen months or more, a significant amount of battery power consumption can occur during this period. In addition, the HCP can be located in a different time zone than the manufacturer and thus, correctly setting the RTC can be further complicated.

Conventionally, manufacturers solve these problems by using a more expensive battery with sufficient power to last the maximum storage duration. Manufacturers also set the RTC based upon the location to which the devices are to be used. Both of these solutions however, require additional manufacturing expense and increase the cost of the medical devices to the end users. Accordingly, improved methods and apparatus are needed to perform setup synchronization of such devices. Further, there are a variety of other configuration options that HCPs can setup on end user medical devices (e.g., BGMs) such as the units used. (e.g., mg/dL vs. mmol/L), high/low limits, reminder alarms, etc.

Embodiments of the present invention provide a setup synchronization apparatus that addresses all of these issues. A setup synchronization apparatus according to embodiments of the present invention can be adapted to wirelessly and automatically set an RTC and other parameters of an end user medical device. Such a setup synchronization apparatus can include a controller (e.g., a programmable microcontroller); a memory for storage of a host computer application; a transceiver (e.g., a transmitter/receiver) that enables wireless communication with the end user medical devices; and a computer interface I/O port such as a universal serial bus (USB) interface for communication with a host computer and to allow uploading/installation of the host computer application to the host computer.

Figure 1:
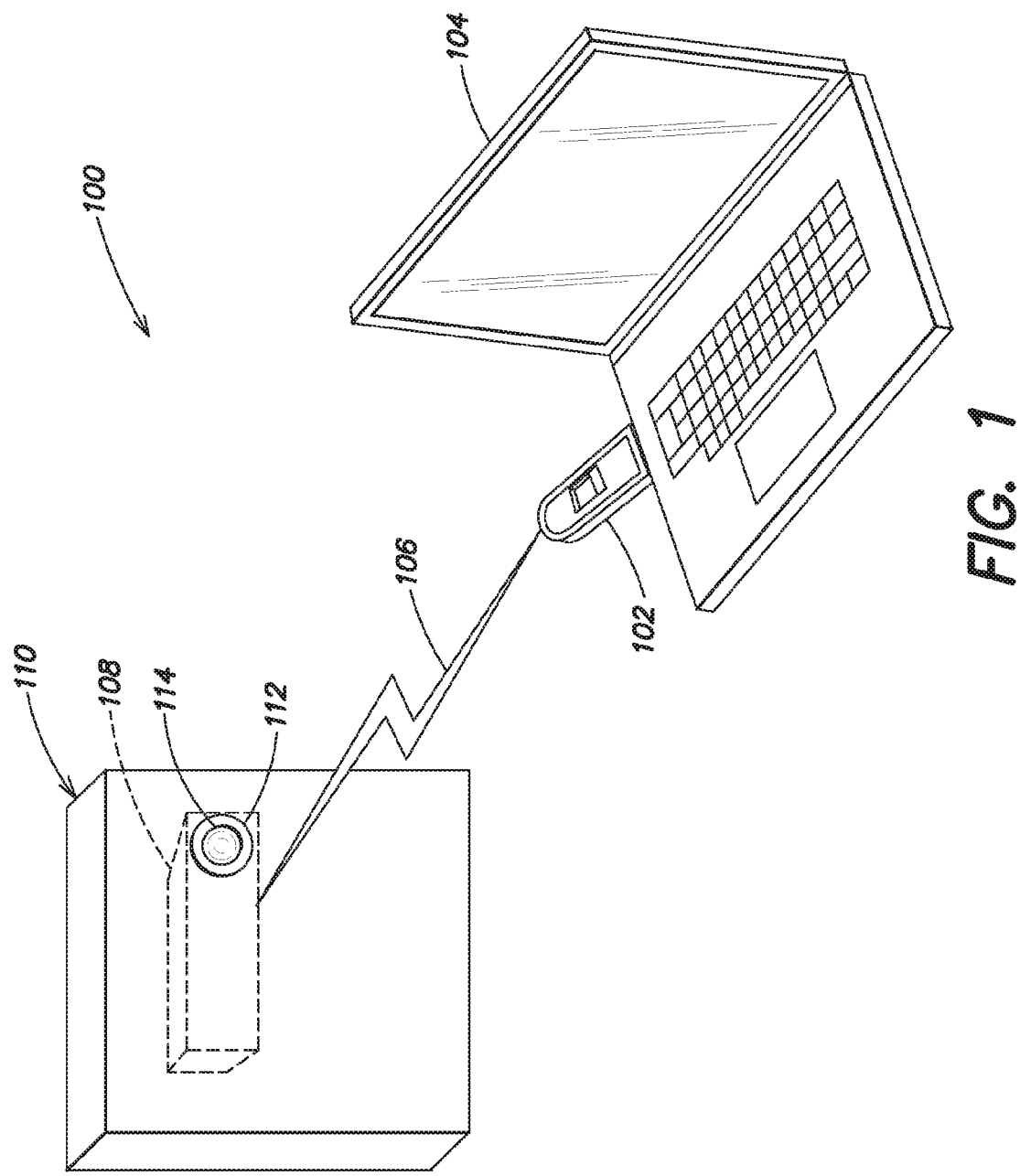
FIG. 1 illustrates a perspective view of an example setup synchronization system according to some embodiments of the present invention.

Turning to FIG. 1, in some embodiments, the system 100 of the present invention includes a setup synchronization apparatus 102 that is adapted to be connected to a host computer 104 operated by a HCP. The setup synchronization apparatus 102 is also adapted to wirelessly communicate 106 with an end user medical device 108 (e.g., a BGM) while the end user medical device 108 is still contained within the packaging 110 from the manufacturer. In some embodiments, the packaging 110 can include an access hole 112 that allows a HCP to trigger an activation function (e.g., press an activation button 114) on the end user medical device 108 while the device 108 is still contained within the packaging 110.

In operation, the setup synchronization apparatus 102 is connected to the host computer 104, for example, via a USB port in the host computer 104. In some embodiments, upon connection to the host computer 104, an application executing on the setup synchronization apparatus 102 checks to see if the host, computer 104 has the host computer application installed. If not, the host computer application can be automatically (or with HCP authorization) installed on the host computer 104.

Once the installation of the host computer application is complete, the host computer application will run in the background of the host computer 104, waiting for a setup synchronization apparatus 102 to request the time and setup parameters. As long as the setup synchronization apparatus 102 is connected to the host computer 104, the setup synchronization apparatus 102 will scan for end user medical devices 108 to synchronize. The host application is operative to provide a user interface to the HCP for configuring parameters of the medical device. The host application can include any number of graphical user interface (GUI) controls to allow the HCP to select parameter values such as time zone, units of measure, warning alarms, target zone levels, operating modes, sampling rates, glucose measurement data, patient information, etc.

In some embodiments, the end user medical device 108 can be shipped in a low power consumption mode (e.g., in a "deep sleep" mode) or in an "off" state. In either case, the RTC within the end user medical device 108 is not running. Pressing the activation button 114 through the packaging access hole 112 triggers an activation function which switches end user medical device 108 to an active mode and/or powers up the device 108 to an "on" state. The end user medical device 108 initializes and begins "advertising" by broadcasting a wireless signal that both uniquely identifies the device 108 and requests synchronization data from any setup synchronization apparatus 102, within the broadcast range. If a setup synchronization apparatus 102 coupled to a host computer 104 is within range, the setup synchronization apparatus 102 and the device 108 establish a wireless connection 106.

Once the end user medical device 108 and the setup synchronization apparatus 102 connect, the medical device 108 receives the correct time and setup parameters from the host application running on the host computer 104 via the wireless connection 106 between the apparatus 102 and the medical device 108. The host computer 104 thereby synchronizes with the end user medical device 108. In some embodiments, once synchronization has completed, a message or other indicia can be displayed on the host computer 104 and/or on a display of the end user medical device 108. In some embodiments, indicator lights or other indicia can be included on the setup synchronization apparatus 102 and/or the end user medical device 108 to indicate the wireless connection status and/or the synchronization status. Upon completion of synchronization, the end user medical device 108 can automatically disconnect from the setup synchronization apparatus 102 and return to a lower power consumption state but with the RTC now running (e.g., a "shallow sleep" mode). The setup synchronization apparatus 102 can return to a scanning state so that a next end user medical device 108 can be synchronized.

Figure 2:
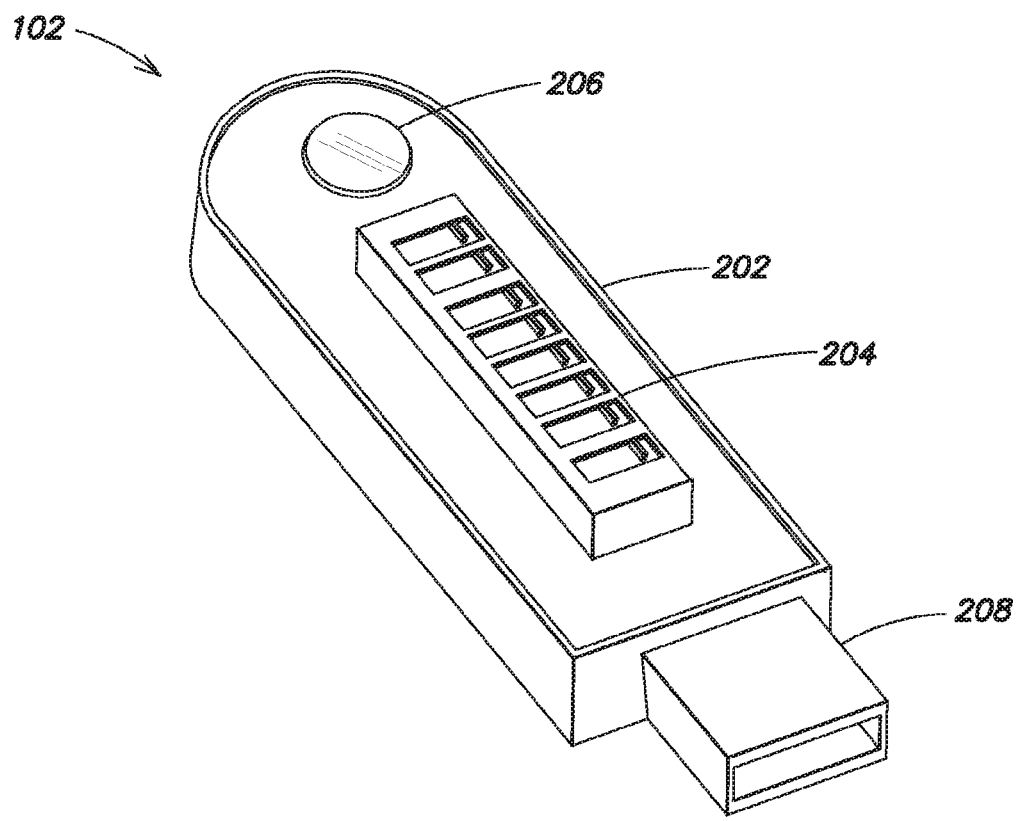
FIG. 2 illustrates a perspective view of an example setup synchronization apparatus according to some embodiments of the present invention.
Figure 3:
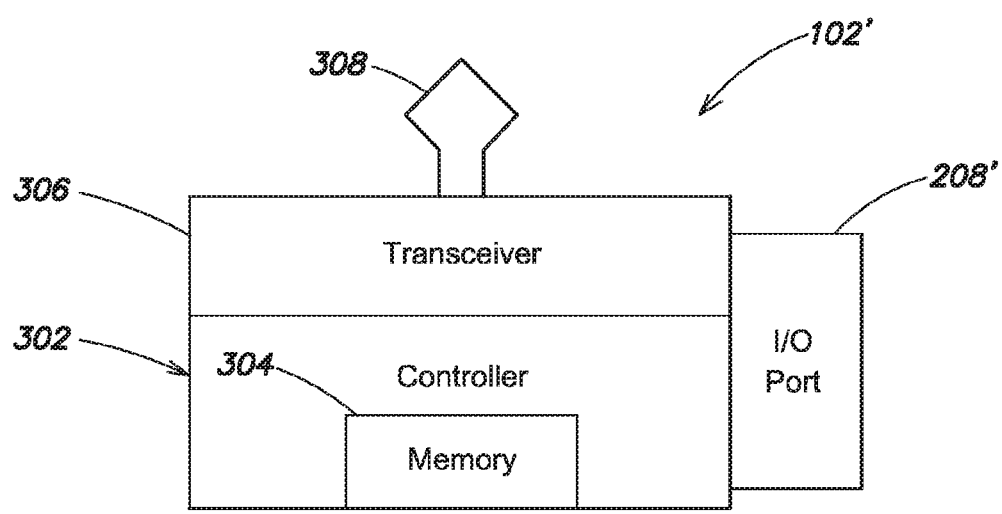
FIG. 3 illustrates a schematic block drawing of a circuit for a setup synchronization apparatus according to some embodiments of the present invention.

Turning now to FIGS. 2 and 3, details of the setup synchronization apparatus 102, are illustrated and described. FIG. 2 depicts a magnified perspective view of an example embodiment of a setup synchronization apparatus 102. The example embodiment includes a housing 202 that encloses and protects a circuit (not visible in FIG. 2 but see FIG. 3). The example setup synchronization apparatus 102 depicted in FIG. 2 also includes configuration switches 204 (e.g., dual in-line package (DIP) switches) for setting certain parameters of the apparatus 102 and an indicator 206 (e.g., a tri-color LED light) that can indicate the status of the setup synchronization apparatus 102.

For example, in some embodiments, the configuration switches 204 can be used to set values for parameters such as time zone, units of measurement, reminder alarms enabled/disabled, etc. that will be passed to end user medical device 108. In some embodiments, the indicator 206 can display different colors to reflect, for example, that the setup synchronization apparatus 102 is (1) scanning for an end user medical device 108 to synchronize, (2) wirelessly connected to an end user medical device 108, or (3) completed synchronizing an end user medical device 108. The example setup synchronization apparatus 102 depicted in FIG. 2 also includes a connector 208 (e.g., a USB connector) for coupling the setup synchronization apparatus 102 to the host computer 104.

FIG. 3 is a block diagram illustrating an example embodiment of a circuit 102' for the setup synchronization apparatus 102. The circuit 102' can include a controller 302 (e.g., a programed microcontroller) operatively coupled to memory 304 (e.g., non-volatile random access memory (NVRAM)) adapted to store instructions for execution by the controller 302 as well as a host computer application. The controller 302 can also be operatively coupled to a transceiver 306 (e.g., a Bluetooth® transceiver, a near field communication (NFC) transceiver, etc.) including an appropriate antennae 308 for wireless communication with end user medical devices 108. Additionally, the circuit 102' can include a host computer interface 208' (e.g., a USB interface) operatively coupled to the controller 302 to enable communication between the setup synchronization apparatus 102 and the host computer 104.

Turning now to FIG. 4, the details of an example embodiment of initial communication between the setup synchronization apparatus 102 and the host computer 104 are illustrated in a block diagram 400. The setup synchronization apparatus 102 is initially connected to the host computer 104 (402) and the setup synchronization apparatus 102 checks the host computer 104 to determine if the host computer application has been installed on the host computer 104 (404). The host computer 104 receives the request and responds (406). If the application has not been installed, the setup synchronization apparatus 102 uploads the application to the host computer 104 (408) and the host computer installs the application (410). Now that the application has been installed, the setup synchronization apparatus 102 begins scanning for an end user medical device 108 to synchronize (412) and the host computer 104 runs the application as a background process (414).

FIG. 5 illustrates an example embodiment of the details of a synchronization process over time. The example depicts the activities of the setup synchronization apparatus 102, the HCP operating the host computer 104 (with a setup synchronization apparatus 102 and associated application installed), and the end user medical device 103 relative to each other as three concurrent interrelated horizontal process flows occurring over time in block diagram 500. Initially, the setup synchronization apparatus 102 is scanning for an end user medical device 108 to synchronize (502) and the end user medical device 108 is in a low power consumption (e.g., deep sleep) mode with the RTC not running (504). Upon the HCP pressing the activation button 114 on the end user medical device 108 (506), the end user medical device 108 begins "advertising" (508) and the setup synchronization apparatus 102 discovers the end user medical device 108 (510). Once a communication connection 106 is established, the setup synchronization apparatus 102 synchronizes with the end user medical device 108 (512) and the end user medical device 108 synchronizes with the setup synchronization apparatus 102 (514). Once the synchronization is complete, the HCP receives a message indicating the completion status (516). The setup synchronization apparatus 102 returns to scanning for another device 108 to synchronize (518) and the end user medical device 108 switches to a low power consumption (e.g., shallow sleep) mode but with the RTC running (520).

Figure 6:
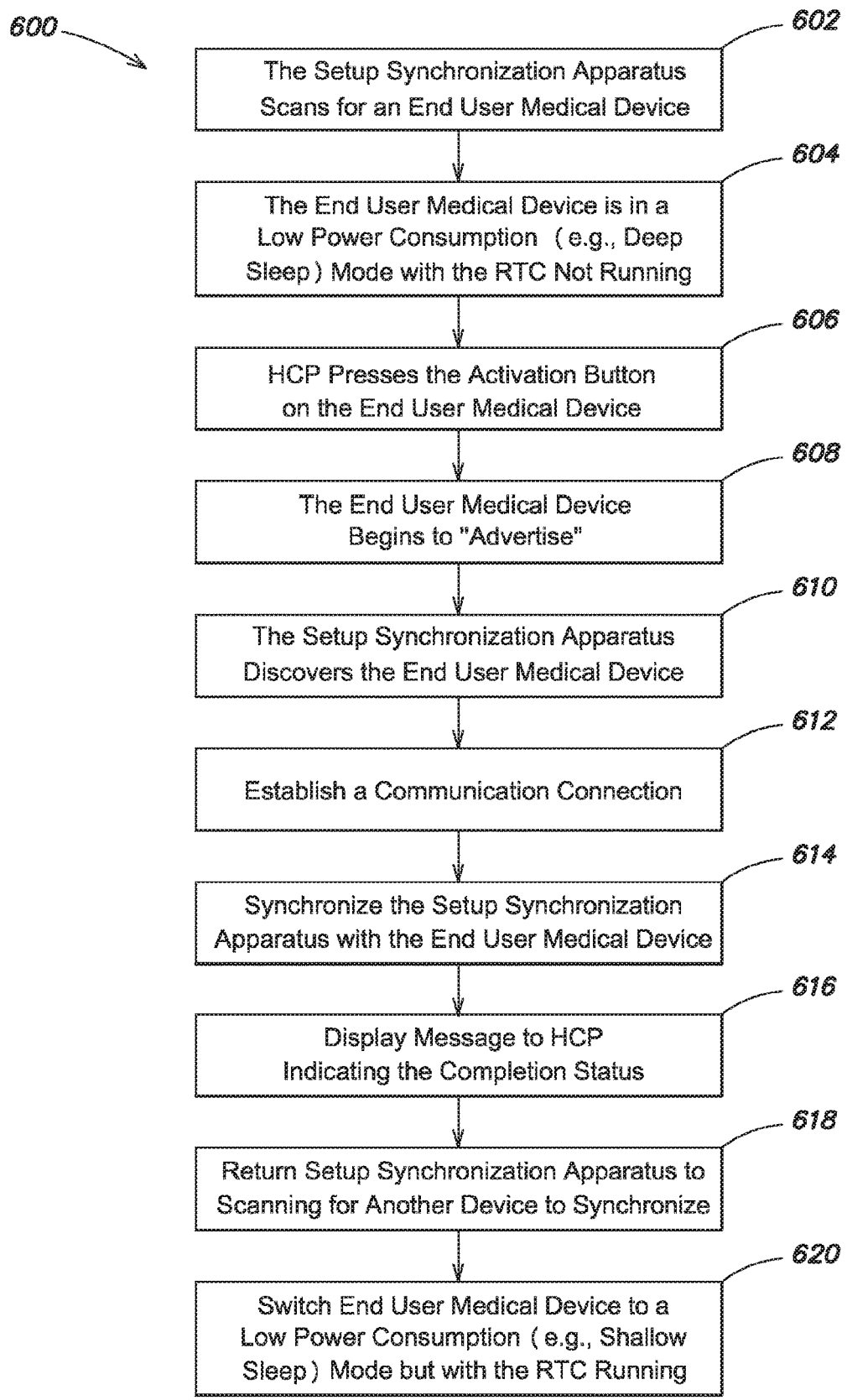
FIG. 6 is a flowchart depicting a method of synchronizing a medical device according to some embodiments of the present invention.

Turning now to FIG. 6, an example method 600 of embodiments of the present invention is depicted in a flowchart. Initially, the setup synchronization apparatus 102 is scanning for an end user medical device 103 to synchronize (602) and the end user medical device 108 is in a low power consumption (e.g., deep sleep) mode with the RTC not running (604). Upon the HCP pressing the activation button 114 on the end user medical device 108 (606), the end user medical device 108 begins "advertising" (608) and the setup synchronization apparatus 102 discovers the end user medical device 108 (610). Once a communication connection 106 is established (612), the setup synchronization apparatus 102 synchronizes with the end user medical device 108 (614). Once the synchronization is complete, the HCP receives a message indicating the completion status (616). The setup synchronization apparatus 102 returns to scanning for another device 108 to synchronize (618) and the end user medical device 108 switches to a low power consumption (e.g., shallow sleep) mode but with the RTC running (620).

The foregoing description discloses only example embodiments of the invention. Modifications of the above-disclosed apparatus, systems and methods which fall within the scope of the invention will be readily apparent to those of ordinary skill in the art. Accordingly, while the present invention has been disclosed in connection with example embodiments, it should be understood that other embodiments may fall within the scope of the invention, as defined by the following claims.

The invention claimed is:

1. An end user medical device comprising:
   a controller and a memory operative to store instructions executable on the controller, the controller and memory operative to:
   perform an activation function to put the end user medical device in an advertising mode for requesting synchronization,
   establish a communications connection with a setup synchronization apparatus,
   receive synchronization data from the setup synchronization apparatus once a communication connection has been established,
   synchronize the end user medical device in accordance with received synchronization data, and
   determine and store medical data of a user;
   a wireless transceiver for transmitting a synchronization request and for receiving synchronization data;
   a manually-operated actuator to cause the controller to perform the activation function;
   a real-time clock, the real-time clock not running prior to the advertising mode for requesting synchronization; and
   a battery to power the controller, wireless transceiver, and real-time clock once running.

2. The end user medical device of claim 1 further comprising packaging sized to contain the end user medical device therein.

3. The end user medical device of claim 2 wherein the packaging has an access hole aligned with the manually-operated actuator to provide access to the manually-operated actuator.

4. The end user medical device of claim 1 wherein the manually-operated actuator is an activation button that can be pressed to cause the controller to perform the activation function.

5. The end user medical device of claim 1 wherein the synchronization data comprises at least one of correct time, time zone, units of measure, operating modes, sampling rates, patient information, and medical data target zones.

6. The end user medical device of claim 1 further comprising a display configured to display a message or other indicia indicating that synchronization has completed.

7. The end user medical device of claim 1 wherein the controller is further operative to disconnect from the setup synchronization apparatus upon completion of synchronization.

8. The end user medical device of claim 1 wherein, upon completion of synchronization, the end user medical device switches to a low power consumption mode with the real-time clock running.

9. The end user medical device of claim 1 wherein the end user medical device comprises a blood glucose meter.

10. A blood glucose meter comprising:
    a controller and a memory operative to store instructions executable on the controller, the controller and memory operative to perform an activation function to put the blood glucose meter in an advertising mode for requesting synchronization and operative to measure and store blood glucose readings of a user;
    a manually-operated actuator to cause the controller to perform the activation function; and
    a real-time clock, the real-time clock not running prior to the advertising mode for requesting synchronization.

11. The blood glucose meter of claim 10 further comprising packaging sized to contain the blood glucose meter therein.

12. The blood glucose meter of claim 11 wherein the packaging has an access hole aligned with the manually operated actuator to provide access to the manually-operated actuator.

13. The blood glucose meter of claim 10 wherein the manually-operated actuator is an activation button that can be pressed to cause the controller to perform the activation function.

14. A method of synchronizing an end user medical device, the method comprising:
performing an activation function in the end user medical device to put the end user medical device in an advertising mode for requesting synchronization;
advertising for synchronization via the end user medical device in the advertising mode, the end user medical device having a real-time clock, the real-time clock not running prior to the advertising for synchronization;
establishing a communication connection between the end user medical device and synchronization apparatus; and
synchronizing the end user medical device in accordance with synchronization data received from the synchronization apparatus.

15. The method of claim 14 further comprising displaying an indication at the end user medical device that the end user medical device has been synchronized.

16. The method of claim 14 wherein the synchronizing comprises setting the real-time clock to the correct time.

17. The method of claim 14 wherein the synchronizing comprises configuring the end user medical device with at least one of a time zone, units of measure, operating modes, sampling rates, patient information, and medical data target zones.

18. The method of claim 14 wherein the performing, the advertising, the establishing, and the synchronizing are performed while the end user medical device is contained within packaging from the manufacturer.

19. The method of claim 14 further comprising shipping from the manufacturer the end user medical device in a low power consumption mode with the real-time clock not running.

20. The method of claim 14 further comprising switching the end user medical device to a low power consumption mode with the real-time clock running upon completion of synchronization.

* * * * *